(12) United States Patent
Wöhrstein et al.

(10) Patent No.: US 10,851,411 B2
(45) Date of Patent: Dec. 1, 2020

(54) MOLECULAR IDENTIFICATION WITH SUBNANOMETER LOCALIZATION ACCURACY

(71) Applicant: Ludwig-Maximilians-Universität München, Munich (DE)

(72) Inventors: Johannes B. Wöhrstein, Altdorf (DE); Kalim Mir, Cambridge, MA (US); Ralf Jungmann, Munich (DE); Florian Schüder, Kaufering (DE)

(73) Assignees: Ludwig-Maximilians-Universität München, Munich (DE); XGenomes Corp., Cambridge, MA (US)

( * ) Notice: Subject to any disclaimer, the term of this patent is extended or adjusted under 35 U.S.C. 154(b) by 132 days.

(21) Appl. No.: 16/071,974

(22) PCT Filed: Feb. 6, 2017

(86) PCT No.: PCT/EP2017/052548
§ 371 (c)(1),
(2) Date: Jul. 23, 2018

(87) PCT Pub. No.: WO2017/134303
PCT Pub. Date: Aug. 10, 2017

(65) Prior Publication Data
US 2019/0024165 A1 Jan. 24, 2019

(30) Foreign Application Priority Data
Feb. 5, 2016 (EP) .................................. 16154448

(51) Int. Cl.
| | | |
|---|---|---|
| *C12Q 1/68* | (2018.01) | |
| *C12Q 1/6874* | (2018.01) | |
| *C12Q 1/6869* | (2018.01) | |
| *C12Q 1/6816* | (2018.01) | |
| *C12Q 1/6834* | (2018.01) | |
| *C12Q 1/6853* | (2018.01) | |
| *G01N 21/64* | (2006.01) | |

(52) U.S. Cl.
CPC ........ *C12Q 1/6874* (2013.01); *C12Q 1/6816* (2013.01); *C12Q 1/6834* (2013.01); *C12Q 1/6853* (2013.01); *C12Q 1/6869* (2013.01); *G01N 21/6428* (2013.01); *C12Q 2521/501* (2013.01); *C12Q 2563/107* (2013.01); *C12Q 2563/179* (2013.01); *C12Q 2563/185* (2013.01); *C12Q 2565/518* (2013.01); *G01N 2021/6439* (2013.01)

(58) Field of Classification Search
None
See application file for complete search history.

(56) References Cited

FOREIGN PATENT DOCUMENTS

| WO | 2013055995 A2 | 4/2013 |
|---|---|---|
| WO | 2013184754 A2 | 12/2013 |
| WO | 2015017759 A1 | 2/2015 |

OTHER PUBLICATIONS

Jungmann, R. et al., "Single-Molecule Kinetics and Super-Resolution Microscopy by Fluorescence Imaging of Transient Binding on DNA Origami." Nano Lett., 2010, 10(11): 4756-4761.
Lin, C. et al., "Submicrometre geometrically encoded fluorescent barcodes self-assembled from DNA." Nature Chemistry, Oct. 2012, 4(10): 832-839.

*Primary Examiner* — James Martinell
(74) *Attorney, Agent, or Firm* — Saliwanchik, Lloyd & Eisenschenk

(57) ABSTRACT

The present invention relates to methods of determining the sequence of nucleotides in target nucleic acid molecules. Thus, the invention relates to methods of sub-unit sequencing. The methods comprise the use of identification nucleic acid detection entities which specifically hybridize to the target nucleic acid, bind identification tags and have localization tags transiently bind thereto.

20 Claims, 8 Drawing Sheets
Specification includes a Sequence Listing.

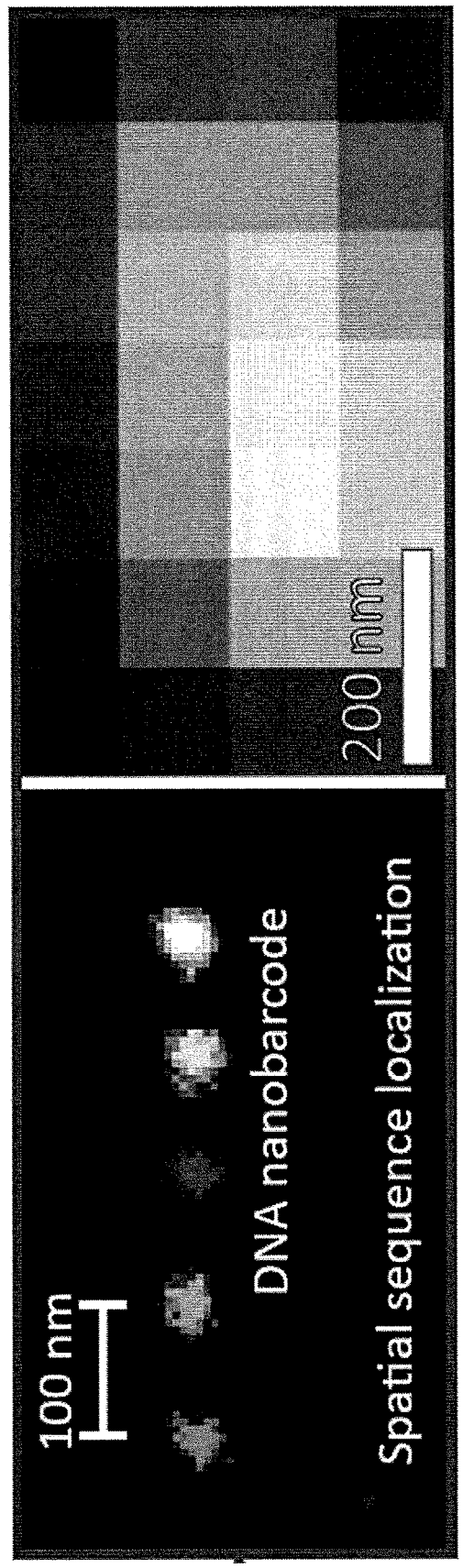
Figure 1 B and C

Figure 7, a.

| Localization Sequence | Localization Tag |
|---|---|
| Partner 1a 5'–TTATACATCTA–3' | Partner 2a 5'–CTAGATGTAT–label |
| Partner 1b 5'–TTATCTACATA–3' | Partner 2b    5'–TATGTAGATC–label |
| Partner 1c 5'–TTTCTTCATTA–3' | Partner 2c 5'–GTAATGAAGA–label |
| Partner 1d 5'–TTATGAATCTA–3' | Partner 2d 5'–GTAGATTCAT–label |
| Partner 1e 5'–TTTTAGGTAAA–3' | Partner 2e 5'–CTTTACCTAA–label |
| Partner 1f 5'–TTAATTGAGTA–3' | Partner 2f 5'–GTACTCAATT–label |
| Partner 1g 5'–TTAATTAGGAT–3' | Partner 2g 5'–CATCCTAATT–label |
| Partner 1h 5'–TTATAATGGAT–3' | Partner 2h 5'–GATCCATTAT–label |
| Partner 1i 5'–TTTAATAAGGT–3' | Partner 2i 5'–CACCTTATTA–label |
| Partner 1j 5'–TTATAGAGAAG–3' | Partner 2j 5'–CCTTCTCTAT–label |
| Partner 1k 5'–TTTTGATGATA–3' | Partner 2k 5'–GTATCATCAA–label |
| Partner 1l 5'–TTATAGTGATT–3' | Partner 2l 5'–GAATCACTAT–label | b.

| TCACAGAGTTGAACGATCCTTTACACAGAGCA | TTATACATCTA | TATGAGGACGAATCTCCCGCTTATA |
|---|---|---|
| Centromere specific probe | Localization sequence | Origami connector |

MOLECULAR IDENTIFICATION WITH SUBNANOMETER LOCALIZATION ACCURACY

CROSS REFERENCE TO RELATED APPLICATIONS

This application is a National Stage Application of International Application Number PCT/EP2017/052548, filed Feb. 6, 2017; which claims priority to European Patent Application No. 16 154 448.1, filed Feb. 5, 2016.

The present invention relates to methods of determining the sequence of nucleotides in target nucleic acid molecules. Thus, the invention relates to methods of sub-unit sequencing. The methods comprise the use of identification nucleic acid detection entities (probes) which specifically hybridize to the target nucleic acid, bind identification tags and have localization tags transiently bind thereto.

BACKGROUND OF THE INVENTION

DNA sequencing has become commonplace in the research and diagnostic fields and is a multi-billion dollar industry. Two of the most commonly used sequencers, HiSeq (Illumina, Inc.) and Ion Torrent™ (Life Technologies, Inc.), rely on amplification and immobilization of DNA fragments onto a solid surface such that molecules of a common ancestor are co-localized. Sequencing-by-synthesis follows, in which enzymatic DNA polymerization using the immobilized DNA fragments as template is coupled to a detection scheme, with fluorescence or release of hydrogen ions used by the aforementioned sequencers, respectively. Other sequencing technology relies on the analysis of single molecules of DNA without the need for PCR amplification, hence providing a simpler workflow. The PacBio RS II system (Pacific Biosciences of California, Inc.) uses phosphate-linked fluorophores of dNTPs to transiently observe nucleotide incorporation on the single-molecule level. However, the error rate of single molecule sequencing methods is high.

Assessing molecular information, such as the composition of biomolecular complexes or polynucleotide and polypeptide sequences is challenging due to two reasons: First, all molecular subunits, i.e. one or multiple consecutive nucleotides, amino acids or protein domains, need to be accurately localized to investigate the spatial organization of a complex or a sequence. Second, these subunits need to be identified. For example, DNA is a polymer which is chemically composed of nucleotide sub-units, which in the human genome, can number from 50 million (shortest chromosome) to 250 million (longest chromosome). As the human genome is diploid, there are two copies of each type of chromosome.

Fluorescence microscopy approaches provide an advantageous toolkit for assessing molecular information since large numbers of molecules can be investigated in parallel in a non-disruptive fashion.

US 2013/026019 A1 describes barcode probes which comprise a target binding moiety and one or more fluorescently labeled nucleic acid nanostructures. The barcode probes are DNA origami structures and they can be used to determine the presence or absence of a target in a sample.

EP 1370690 A2 and EP 1556506 A1 describe a method for sequencing comprising hybridization or ligation of a repertoire of oligonucleotide probes to polynucleotides stretched on a surface.

WO 2013/055995 A2 describes a method of sequencing nucleic acids by structure assembly using sequencing by ligation and/or sequencing by hybridization. Said method comprises the use of oligonucleotide probes having template hybridizing nucleic acid sequences and barcode having detectable moieties to identify a nucleotide at a position in the oligonucleotide probe and its complementary nucleotide in a template DNA.

WO 2013/184754 A2 describes a method of sequencing nucleic acids using sequencing primer and oligonucleotide probes. The oligonucleotide probes are attached to a barcode, a spatially distinct nucleic acid structure (e.g. DNA origami) corresponding to one or more nucleotides in the oligonucleotide probe and detectable label.

Lin et al. (2012) disclose DNA-origami technology in the construction of submicrometre nanorods that act as fluorescent barcodes. The authors show that spatial control over the positioning of fluorophores on the surface of a stiff DNA nanorod can produce 216 distinct barcodes that can be decoded unambiguously using epifluorescence or total internal reflection fluorescence microscopy. Barcodes with higher spatial information density were demonstrated via the construction of super-resolution barcodes with features spaced by ~40 nm. One species of the barcodes was used to tag yeast surface receptors, which suggests their potential applications as in situ imaging probes for diverse biomolecular and cellular entities in their native environments.

Jungmann et al. (2014) describe the transient binding of short fluorescently labeled oligonucleotides (DNA-PAINT, a variation of point accumulation for imaging in nanoscale topography) for multiplexed super-resolution imaging that achieves sub-10-nm spatial resolution in vitro on synthetic DNA structures. The authors also describe a multiplexing approach (Exchange-PAINT) that allows sequential imaging of multiple targets using only a single dye and a single laser source. They experimentally demonstrate ten-color super-resolution imaging in vitro on synthetic DNA structures as well as four-color two-dimensional (2D) imaging and three-color 3D imaging of proteins in fixed cells.

There is a need in the art for technological developments that can precisely locate nucleotide sub-units on single genomic DNA molecules (derived from one of the two homologous chromosomes) in order to phase haplotypes and precisely determine the genetic influence of DNA sequence variations. Moreover, it is important to make accurate localizations along long stretches of DNA (in the 100,000 to million base range so that structural diversity and aberrations (copy number variation, translocations) can be readily determined.

Thus, there is a need for improved spatial localization and molecular identification means and methods, in particular for nanometric spatial localization and sub-unit sequencing means and methods.

SUMMARY OF THE INVENTION

According to the present invention this object is solved by a method of determining the sequence of nucleotides in a target nucleic acid molecule, comprising the steps of:
(1) providing a target nucleic acid molecule,
   wherein copies of said target nucleic acid molecule are immobilized on a solid substrate,
(2) providing a plurality of nucleic acid detection entities, wherein each nucleic acid detection entity is at least in part single stranded and comprises:
   (i) a specific probe nucleotide sequence,
   (ii) a localization nucleotide sequence, and
   (iii) an identification nucleotide sequence, (3) providing a plurality of identification tags,
  wherein each identification tag
    is specific for a specific probe nucleotide sequence (i) of the nucleic acid detection entity, and
    comprises a nucleotide sequence complementary to the identification nucleotide sequence (iii) of the nucleic acid detection entity,
  wherein, preferably, each identification tag is or can be detectably labelled, e.g. via a fluorophore,
(4) providing a plurality of localization tags,
  wherein said localization tag comprises
    a nucleotide sequence complementary to the localization nucleotide sequence (ii) of the nucleic acid detection entity).
(5) hybridizing and optionally ligating the nucleic acid detection entities to the single stranded target nucleic acid molecules, preferably hybridizing the nucleic acid detection entities to the single stranded target nucleic acid molecules and optionally ligating the nucleic acid detection entities to a nucleic annealed to the single stranded target nucleic acids,
(6) hybridizing the identification tags to the identification nucleotide sequence (iii) of the nucleic acid detection entities,
  optionally, stretching and/or aligning the identification markers, wherein, preferably, the identification markers are the identification nucleotide sequence to which identification tags are hybridized,
(7) detecting the identification tags, preferably the detectably labelled identification tags,
  preferably via fluorescence microscopy,
  alternatively, via high-resolution microscopy,
(8) transiently hybridizing the localization tags, preferably the detectably labelled localization tags, to the localization nucleotide sequence (ii) of the nucleic acid detection entities and detecting said transient hybridization,
  preferably via fluorescence microscopy,
  alternatively, via high-resolution microscopy,
  and
(9) spatially detecting and identifying the nucleic acid sequence, preferably specific nucleic acid sequences in the target nucleic acid molecules.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "20 to 30 nucleotides" should be interpreted to include not only the explicitly recited values of 20 to 30, but also include individual values and sub-ranges within the indicated range. Thus, included in this numerical range are individual values such as 20, 21, 22 . . . 28, 29, 30 and sub-ranges such as from 22 to 25, from 20 to 28, etc. This same principle applies to ranges reciting only one numerical value, such as "at least 10 times". Furthermore, such an interpretation should apply regardless of the breadth of the range or the characteristics being described.

The present invention provides a method of determining the sequence of a target nucleic acid molecule.

In particular, the present invention provides a method of determining the sequence of nucleotides in a target nucleic acid molecule, i.e. a sub-unit sequencing method.

The method of the present invention comprises the steps of:
(1) providing a target nucleic acid molecule,
  wherein copies of the target nucleic acid molecule are immobilized on a solid substrate,
(2) providing a plurality of nucleic acid detection entities, wherein each nucleic acid detection entity is at least in part single stranded and comprises:
  (i) a specific probe nucleotide sequence,
  (ii) a localization nucleotide sequence
    for transient binding of a localization tag,
  (iii) an identification nucleotide sequence
    for stable hybridization with an identification tag specific for the specific probe nucleotide sequence (i),
(3) providing a plurality of identification tags,
  wherein each identification tag
    is specific for a specific probe nucleotide sequence (i) of the nucleic acid detection entity, and
    comprises a nucleotide sequence complementary to the identification nucleotide sequence (iii) of the nucleic acid detection entity, wherein, preferably, each identification tag is or can be detectably labelled, e.g. via a fluorophore,
(4) providing a plurality of localization tags,
  wherein said localization tag comprises
    a nucleotide sequence complementary to the localization nucleotide sequence (ii) of the nucleic acid detection entity.
(5) hybridizing and optionally ligating the nucleic acid detection entities to the single stranded target nucleic acid molecules, preferably hybridizing the nucleic acid detection entities to the single stranded target nucleic acid molecules and optionally ligating the nucleic acid detection entities to a nucleic acid annealed to the single stranded target nucleic acid,
(6) hybridizing the identification tags to the identification nucleotide sequence (iii) of the nucleic acid detection entities,
  optionally, stretching and/or aligning the identification markers, wherein, preferably, the identification markers are the identification nucleotide sequence to which identification tags are hybridized,
(7) detecting the identification tags, preferably the detectably labelled identification tags,
  preferably via fluorescence microscopy, alternatively, via high-resolution microscopy,
(8) transiently hybridizing the localization tags, preferably the detectably labelled localization tags, to the localization nucleotide sequence (ii) of the nucleic acid detection entities and detecting said transient hybridization, preferably via fluorescence microscopy,
alternatively, via high-resolution microscopy,
and
(9) spatially detecting and identifying the nucleic acid sequence in the target nucleic acid molecules.

Step (1)

In step (1) of the method of the invention, the target nucleic acid molecule is provided.

The term "target nucleic acid molecule" and "template" are used interchangeably in this application and refer to the nucleic acid molecule whose nucleotide sequence is to be determined by the method of the present invention, The target nucleic acid molecule may comprise dsDNA, ssDNA, dsRNA, ssRNA, or a chimera or mimic thereof Preferably, multiple copies, i.e. a plurality of copies, of the target nucleic acid molecule are provided.

Said copies of the target nucleic acid molecule are immobilized on a solid substrate or support.

In one embodiment, the solid substrate is selected from glass, silicon, silicon dioxide, polydimethoxysilane (PDMS), polymer (e.g. polystyrene, cyclic olefin, zeonex, poly(methyl methacrylate), and metal, e.g. gold.

In one embodiment, the target nucleic acid molecule is attached or immobilized to the solid substrate via biotin/streptavidin.

For example, the target nucleic acid molecule is biotinylated (such as at its 5' end or 3' end) and is attached to a streptavidin-coated surface of the solid substrate. The biotinylation can be achieved at the 3' end by tailing with biotinylated nucleotide using a terminal transferase.

In one embodiment, the target nucleic acid molecule is attached or immobilized to the solid substrate via chemical linking, such as amine, thiol, and/or covalent surface chemistry.

In one embodiment, the target nucleic acid molecule is attached or immobilized to the solid substrate via molecular combing.

In one embodiment, the substrate is pre-coated with a chemical or biological coating.

In one embodiment, the target nucleic acid molecule is attached or immobilized to the solid substrate via electrostatic interaction.

In a preferred embodiment, the copies of the target nucleic acid molecule are immobilized on the solid stretched, preferably stretched and parallel to each other.

Preferably, the copies of the target nucleic acid molecule are stretched.
 (a) randomly but aligned in a parallel orientation,
   e.g. by applying an electric field;
 (b) in the form of a DNA curtain;
 (c) randomly; (d) via molecular combing.
 (e) via flow stretching; or
 (f) via nano-confinement Preferably, the target nucleic acid molecule is stretched by flow or electrophoretic stretching, rendering the molecules in parallel orientation.

DNA curtains have been described in the art and are suitable for the method of the invention as well (see e.g. Sternberg et al., 2014).

In some embodiments, where double-stranded target nucleic acid molecules are provided, they are rendered into single stranded target nucleic acid molecules, preferably fully or partially single stranded target nucleic acid molecules.

Preferably, the double-stranded target nucleic acid molecules are rendered into single stranded target nucleic acid molecules as part of step (1), more preferably before the stretching. In some embodiments, it can also be done after the stretching.

The skilled artisan knows how to render double-stranded nucleic acid molecules into single stranded nucleic acid molecules.

Examples are:
use of enzymes, such as helicases or exonucleases
melting the double strand by applying higher temperatures (heat denaturation) (such as in a PCR), or chemical denaturation.

In some embodiments, where double-stranded target nucleic acid molecules are provided, they are nicked at a plurality of sites.

Step (2)

In step (2) of the method of the invention, nucleic acid detection entities are provided.

A plurality of nucleic acid detection entities is provided.

A "plurality" of nucleic acid detection entities as used herein refers to at least two of said entities.

Typically, more than about 100 different nucleic acid detection entities (and, thus, also identification tags) are provided and used in the method of the invention.

For example, a sequence of 6 nucleotides in the target nucleic acid is interrogated by the nucleic acid detection entities (and probed by their respective specific probe nucleotide sequence). Hereby, 4096 different detection nucleic acid detection entities and thus also 4096 different identification tags (barcodes) are necessary. In another example, a sequence of 5 nucleotides on the target nucleic acid is interrogated by the nucleic acid detection entities, then 1024 different detection nucleic acid detection entities and thus also 1024 different identification tags (barcodes) are necessary.

In another example, a sequence of 4 nucleotides on the target nucleic acid is interrogated by the nucleic acid detection entities, then 256 different detection nucleic acid detection entities and thus also 256 different identification tags (barcodes) are necessary. In case that one nucleotide is interrogatedtested/scanned, 4 nucleic acid detection entities and identification tags are needed (A, C, G, T).

Each nucleic acid detection entity is at least in part single stranded.

Each nucleic acid detection entity comprises or consists of:
 (i) a specific probe nucleotide sequence,
 (ii) a localization nucleotide sequence for transient binding of a localization tag, and
 (iii) an identification nucleotide sequence for stable hybridization with an identification tag specific for the specific nucleic acid sequence (i),
 (i) Specific Probe Nucleotide Sequence (i)

The specific nucleotide sequence (i) or "probe sequence" or "specific probe nucleotide sequence" or "specific capture nucleotide sequence" or "capture sequence" is single-stranded.

The specific nucleotide sequence (i) will specifically hybridize to its complementary nucleotide sequence on the target nucleic acid molecule, if present.

The terms "capture sequence" or "capture nucleotide sequence" or "specific capture nucleotide sequence", as used herein, are meant to refer to a sequence which is used for probing another sequence. For this reason these terms are also used herein interchangeably with the terms "probe sequence" or "probe nucleotide sequence" or "specific probe nucleotide sequence".

The specific nucleotide sequence (i) has preferably a length of about 3 to 30 nucleotides, preferably about 4 to 10 nucleotides, such as about 5 or 6 nucleotides.

The plurality of specific nucleotide sequences (of the plurality of nucleic acid detection entities) covers the whole sequence space. For example, with a length of 4 nucleotides, $4^4=256$ different sequences will need to be present. The same number of unambiguous identification tags is required, as well as orthogonal identification nucleotide sequences (iii).

(ii) Localization Nucleotide Sequence

The localization nucleotide sequence is for the transient binding of a localization tag.

The localization nucleotide sequence comprises a single stranded nucleic acid stretch with a specific sequence for transient binding of a localization tag. Preferably the transiently binding localization tag is complementary to the localization nucleotide sequence.

In one embodiment, the localization nucleotide sequence is part of the same nucleic acid structure as the probe sequence (i) or is attached to probe sequence (i), e.g. by hybridization.

In one embodiment, the localization nucleotide sequence can be replaced or further comprise a localization entity or tag, such as
  fluorophore(s) or a photoactive particle(s),
  detectable (nano)particle(s),
    such as metal (nano)particle(s), e.g. gold,
    quantum dot(s), or
    combinations thereof;

In one embodiment, the localization nucleotide sequence can be replaced or further comprise a localization entity or tag, such as an entity that can be localized with sub 10 nm accuracy.

(iii) Identification Nucleotide Sequence

The identification nucleotide sequence (iii) is for the stable hybridization with an identification tag specific for the specific nucleic acid sequence (i).

The identification nucleotide sequence (iii) of a nucleic acid detection entity has preferably a length of about 5 to 100 nucleotides, preferably about 10 to 100 nucleotides, more preferably about 15 to 50 nucleotides.

The identification nucleotide sequence (iii) is preferably longer than the probe sequence (i). This allows stable hybridization of the identification tag and increases the sequence space, so that an orthogonal sequence for every identification tag can be designed.

As explained above, the same number of unambiguous identification tags is needed as the number of specific probe sequences (i)) and the number of identification nucleotide sequences (iii).

Further Components

In further embodiments, the nucleic acid detection entities can comprise further components, such as small molecule tag(s), or can be made of any of:
  Antibody, nanobody, VHH antibody, aptamer, and combinations thereof In one embodiment, the nucleic acid detection entities are replaced with non-nucleic acid detection entities.

In one embodiment, the nucleotide detection entities spatially label a plurality of sites in the target nucleic acid.

In one embodiment, the plurality of labelled sites shows the long-range structure of nucleic acid.

In one embodiment, the long-range structure of nucleic acid can be used to determine the identity of the nucleic acid or to detect structural variation between the nucleic acid and another nucleic acid.

In one embodiment, after imaging, the location and lengths of the plurality of nucleic acids and the location and identity of nucleic acid detection entities bound thereon are extracted from the images and stored in a computer memory.

In one embodiment, the data extracted after imaging, e.g. the location and lengths of the pluralities of nucleic acids and the location and identity of nucleic acid detection entities, are used to assemble nucleic acid sequence or report on the identity or structure of nucleic acids in a sample In some embodiments, the nucleic acid detection entities, comprising for example DNA Origami can be bound to the target nucleic acids either before or after stretching of the target nucleic acid(s).

The detectable (e.g. fluorescent) labels can be associated with the nucleic acid detection entities in one of the following ways:
  1) fluorescently labelled oligonucleotides are integrated into origami prior to use in identification
  2) fluorescently labelled oligonucleotides are hybridized to DNA origami prior to use in identification
  3) fluorescently labelled oligonucleotides are hybridized to origami after the origami (as part of the nucleic acid identification entity is bound to the target nucleic acid.

In some embodiments, the origami can be directly (e.g. covalently) connected to the probe before the nucleic acid detection entity is bound to the target nucleic acid. Alternatively, the nucleic acid detection entity is modular and the probe module is bound to the target nucleic acid before, the origami module is bound to a docking site associated with the probe.

In this modular system, the localization sequence may be attached to the probe. Optionally the localization can be conducted before the origami module is bound to the probe-localization module. Alternatively, the localization module may be attached to the origami module; hence the probe is bound to the target nucleic acid first followed by the localization ad origami module In one embodiment the origami is aligned in a direction parallel to the target nucleic acid (as shown in FIG. 1). In some embodiments the origami appears to be along the axis of the target nucleic acid. This can be achieved by applying flow stretching, molecular combing stretching or electrophoretic stretching in the same axis as the stretching of the target nucleic acid.

In some embodiments the origami stretched some degrees from the axis of the target molecule, including up to 90 degrees. This can be achieved by applying flow stretching, molecular combing stretching or electrophoretic stretching in a different axis than the stretching of the target nucleic acid. The origami are all ostensibly stretched in the same direction. In some embodiments the features of the origami are super resolved.

In some embodiments the nucleic acid detection elements are hybridized to the target but no ligation is conducted. In some embodiments ligation is conducted. The template can be rendered in a number of different ways for ligation to be conducted. In some embodiments, the target nucleic acid is ostensibly single stranded and the probes of two nucleic acid detection entities bind to the target single stranded nucleic acid in juxtaposition or tandem; when the end of one of the tandem probes is a free 3' OH and the adjacent end of the other tandem probe is a 5' phosphate ligation can occur when a suitable ligase and appropriate buffer conditions and co-factor are provided. This allows sequence to be detected with high specificity and confidence and the localization can be determined very precisely, because two independent measurements are conducted for identification and localization. In some embodiments only one ligating entity is the nucleic acid detection entity, while the other is a probe that does not bear an identification part.

In some embodiments the DNA is partially double stranded and comprises single stranded gaps. These gaps can be created by first nicking the double stranded DNA (using DNAse1 for example), and then gaps are either created by fraying of the ends of the 5' and 3' end of the nicks e.g. due to heating and/or composition of buffer (low salt, Formamide, DMSO etc) or by recessing from the nicks using a 3' or 5 exonuclease activity of an exonuclease or a DNA polymerase. After the ligation any remaining gap can be refilled by a DNA polymerase and dNTPS. The gap filling reaction can also proceed simultaneously with ligation, as is done in the Gap-fill Ligation technique. The ligation and gap filling can be done in solution, before the target nucleic acid is stretched in the surface. The resulting substantially double stranded target nucleic acid structure gives robust, relatively uniform stretching which is conducive to accurately determining distances between the binding positions of the nucleic acid detection entities.

The nucleic acid detection entity may form a padlock probe, with the structure: probe 1-localization/identification parts-probe 2. When both probe 1 and probe 2 are bound to the target nucleic acid at the appropriate locations, a ligase enzyme can join the free ends of probe 1 to probe 2 together.

Step (3)

Identification Tag

In step (2) of the method of the invention, identification tags are provided.

A plurality of identification tags is provided.

A "plurality" of identification tags as used herein refers to at least two of said tags.

Typically and as explained above, more than about 100 different nucleic acid detection entities and, thus, also identification tags are provided and used in the method of the invention.

According to the present invention, each identification tag is specific for a specific capture nucleotide sequence (i) of the nucleic acid detection entity.

Furthermore, each identification tag comprises a nucleotide sequence complementary to the identification nucleotide sequence (iii) of the nucleic acid detection entity.

According to the invention, the identification tag stably hybridizes to the nucleotide sequence of the identification nucleotide sequence (iii) of the nucleic acid detection entity.

As explained above, the same number of unambiguous identification tags (as number of specific capture sequences (i) as identification nucleotide sequences (iii)) is required in the method of the invention.

Preferably and depending on the label(s) or marker(s) used, the identification tags can be detected, analyzed and identified using a fluorescence microscope.

According to the invention, the identification tags preferably come in a variety of unambiguously identifiable forms (i.e. barcodes) where each form corresponds to and thus identifies exactly one capture sequence.

Preferably, the identification tags are based on DNA origami.

Preferably the DNA origami are labelled DNA origami probes, such as DNA origami molecules with a (fluorescence) barcode.

The plurality of unambiguous identification tags can be realized by

1. Geometric Barcoding

Hereby several (spectrally distinct) fluorescent spots are arranged on the tag in specific order. For example, a RED-GREEN-BLUE tag might correspond to the capture sequence "ACT" and will be distinguishable from a YELLOW-GREEN-RED tag which might correspond to "GCA". More complex geometric barcodes are based on a multidimensional arrangement of the fluorescent spots.

For references, see e.g. Lin et al., 2012 or Jungmann et al., 2010.

2. Intensity Based Barcodes

Examples are beads or comparable carriers with a multitude of fluorescent particles.

3. Spectral Barcodes

Examples are red/Green/Blue fluorescent particles, e.g. quantum dots, Fluorospheres or Luminex beads 4. Kinetic Barcodes.

Here fluorescently labeled, short nucleic acid strands transiently hybridize to a complementary strand on the barcode entity (compare to the localization tag). The kinetic of this apparent blinking (frequency/off-time, on-time, intensity) can be tuned by adjusting the labeled nucleic acid concentration, s, the sequence, the sequence length, the chemistry of the sequence (e.g. whether it comprises nucleotide analogue that is more or less stable), the presence of a stabilizing tether (e.g. Stillbene, Spermidine) the number of complementary strands on the barcode entity.

In a preferred embodiment, the identification tags are labelled DNA origami barcodes.

The term "DNA origami" or "DNA origami molecular self-assembly", as used herein, refers to intramolecular folding of a single-stranded DNA scaffold molecule with DNA staple or helper oligonucleotides into a specific molecular structure.

DNA origami structures incorporate DNA as a building material to make nanoscale shapes. In general, the DNA origami process involves the folding of one or more long, "scaffold" DNA strands into a particular shape using a plurality of rationally designed "staple" or "helper" DNA or oligonucleotide strands. The sequences of the staple or "helper" strands are designed such that they hybridize to particular portions of the scaffold strands and, in doing so, force the scaffold strands into a particular shape.

Methods useful in the making of DNA origami structures can be found, for example, in Rothemund 2006, Douglas et al., 2009; Dietz et al, 2009 or U.S. Pat. No. 7,842,793 B2 (Rothemund). Staple design can be facilitated using, for example, CADnano software, available at http://www.cadnano.org.

Now, to these structurally complex DNA nano-structures, fluorescent molecules can be attached at desired locations or spots. Thus, origami technology can be used to generate a large pool of barcodes out of only a few fluorescent molecules.

For references, see e.g. Lin et al., 2012 or Jungmann et al., 2010.

Step (4)

In step (4) of the method of the invention, localization tags are provided.

In one embodiment, a plurality of localization tags is provided.

In a preferred embodiment, a plurality of identical localization tags is provided.

According to the invention, each localization tag comprises a nucleotide sequence complementary to the localization nucleotide sequence (ii) of the nucleic acid detection entity.

According to the invention, the localization tag transiently hybridizes to the localization nucleotide sequence (ii) of the nucleic acid detection entity.

According to the invention, each localization tag further comprises marker(s) or label(s).

Said marker(s) or label(s) are:
fluorophore(s),
   such as an ATTO dye, a Cyanine dye, a deep red dye, or other organic fluorophore,
detectable (nano)particle(s)
   such as metal (nano)particle(s)
      e.g. gold,
quantum dot(s), or
combinations thereof.

In the preferred embodiment, where a plurality of identical localization tags is provided, each of the localization tags comprises the same marker or label and the same nucleotide sequence complementary to the localization nucleotide sequence (ii) of the nucleic acid detection entity.

Step (5)

In step (5) of the method of the present invention, the nucleic acid detection entities are hybridized and optionally ligated to the single stranded target nucleic acid molecules.

After hybridization, the nucleic acid detection entities need to be stably attached to the target sequence. This can be achieved by long enough sequences, stable nucleotide analogues, nucleoeitde tethers such as Stillbene or Spermine, low temperatures, optimized buffer conditions (e.g. high salt). The skilled artisan is able to test and optimize these conditions and parameters.

In an embodiment, for example, where the nucleic acid detection entity is too short for stable hybridization, the entities are ligated upon target nucleic acid molecules.

For example, the detection entity can be enzymatically coupled to the target. In some embodiments, the ligation occurs upon a single stranded target between two oligonucleotides (one of which is the nucleic acid detection entity). In some embodiments both ligating oligonucleotides are nucleic acid detection entities.

In some embodiments the ligation occurs between the 3' or 5' end of a nick in a substantially double stranded target. In some embodiments the ligation occurs within a gap between nicks.

On one embodiment, step (5) comprises the use of a guide RNA, and a cas protein (or other CRISPR type system.

Step (6)

In step (6) of the method of the present invention, the identification tags are hybridized to the identification nucleotide sequence (iii) of the nucleic acid detection entities.

In step (6), the identification tags are optionally stretched and/or aligned.

In some embodiment the identification tags are aligned parallel to the target polynucleotides. In other embodiments the identification tags are aligned perpendicular to the target polynucleotide.

In one embodiment, in step (6), the identification markers are, optionally, stretched and/or aligned, wherein the term "identification marker" refers to the identification nucleotide sequence on its own or the identification nucleotide sequence to which the identification tags are hybridized.

Step (7)

In step (7) of the method of the present invention, the identification tags are detected.

Said detection depends on the label or marker on the identification tags used.

Said detection is preferably via fluorescence microscopy or alternatively, via high-resolution or super-resolution microscopy.

The term "super-resolution microscopy" refers to a fat ii of light microscopy. Super-resolution techniques allow the capture of images with a higher resolution than the diffraction limit They fall into two broad categories: "true" super-resolution techniques, which capture information contained in evanescent waves, and "functional" super-resolution techniques, which use experimental techniques and known limitations on the matter being imaged to reconstruct a super-resolution image. In one embodiment, super-resolution microscopy allows single molecule localization. Such super-resolution microscopy is therefore also sometimes referred to as "single molecule localization microscopy".

True subwavelength imaging techniques include those that utilize the Pendry Superlens and near field scanning optical microscopy, the 4Pi Microscope and structured illumination microscopy technologies like SIM and SMI. However, the majority of techniques of importance in biological imaging fall into the functional category.

There are two major groups of methods for functional super-resolution microscopy: Deterministic super-resolution: The most commonly used emitters in biological microscopy, fluorophores, show a nonlinear response to excitation, and this nonlinear response can be exploited to enhance resolution. These methods include STED, GSD, RESOLFT and SSIM.

Stochastic super-resolution: The chemical complexity of many molecular light sources gives them a complex temporal behavior, which can be used to make several close-by fluorophores emit light at separate times and thereby become resolvable in time. These methods include SOFI and all single-molecule localization methods (SMLM) such as SPDM, SPDMphymod, PALM, FPALM, STORM and dSTORM.

Stochastic super-resolution microscopy can also be performed using techniques based on Points Accumulation in Nanoscale Topography (PAINT). An extension of this approach is called DNA-PAINT, which is based on the molecular recognition capability of DNA molecules to perform super-resolution microscopy. In DNA-PAINT, stochastic switching between fluorescence on- and off-states is facilitated by repetitive, transient binding of short fluorescently labelled oligonucleotides ("imager" strands) to complementary "docking" strands. Upon binding of an imager strand, its fluorescence emission is detected and subsequently localized for super-resolution reconstruction.

Step (8)

In step (8) of the method of the present invention, the localization tags are transiently hybridized to the localization nucleotide sequence (ii) of the nucleic acid detection entities.

In step (8) of the method of the present invention, furthermore said transient hybridization is detected.

Said detection depends on the label or marker associated with the localization tag(s) used.

Said detection is preferably via fluorescence microscopy or alternatively, via high-resolution or single molecule localization microscopy.

Localization tags are detected using a suitable set-up and the positions of the nucleic acid detection entities are thus known with nanometer accuracy.

Step (9)

In step (9) of the method of the present invention, the nucleic acid sequence in the target nucleic acid molecules is spatially detected and identified/determined.

The term "spatially detecting", as used herein, is meant to refer to an act of or acts of "detecting" and "spatially locating". These may occur simultaneously together, one after the other, or in an overlapping manner.

The localization tags determine the close to exact position of the probe sequence, where the identification tag yields the corresponding sequence.

See e.g. FIG. 1.

Preferably, the accuracy or resolution limit of the method is up to about 1 nm, or better than 1 nm. Compare to FIONA (Fluorescence imaging with one nanometer accuracy) (see Yildiz and Selvin, 2005)

Further Description of Preferred Embodiments

The invention discloses a next generation sequencing method in combination with high resolution microscopy and single molecule localization (according to methods known in the art e.g. Jungmann et al).

The method disclosed in the present invention uses the transient binding of a short fluorescently labeled DNA strand (localization tag) to a complementary handle/docking (localization sequence) strand, which is attached to the subunit under investigation for localization. A distinct fluorophore, optically detectable particle or molecular barcode is used for subunit identification.

One preferred embodiment presented herein is nucleic acid sequencing, i.e. the determination of the sequence of a strand of genomic DNA. Here, the goal is to know the identity of every single nucleotide (A, C, G or T) and the order of every single nucleotide, the molecular subunit, as shown FIG. 1b.

The present invention allows for the nanometric spatial localization and identification of sub-units via specific targeting by a transducer molecule (i.e. nucleic acid sequence, small molecule tag, antibody/nanobody/aptamer).

The transducer molecule can bind two entities:
(1) Identification tag or marker (i.e. a fluorophore of a distinct wavelength and/or lifetime or a molecular barcode such as a self-assembled nanostructure which bears color, intensity, kinetic, geometrical etc. encoding);
(2) Localization tag or marker (i.e. target for localization microscopy, such as a fluorophore, quantum dot, nucleic acid for transient localization microscopy).

In one embodiment:
Stretched M13 (double-stranded dumbed-down single helix bundle origami) DNA molecule
  "Start" labeled by biotinylated DNA molecule for initial binding
  Either flow or electrophoretic stretching
  Subsequent "End" labeling by second biotinylated DNA molecule for "locking in place" onto a streptavidin coated substrate
  Potentially intermediate Biotin-streptavidin interactions for efficient "fixation"
  Certain "target" sequences of the single stranded M13 molecule are labeled with the "transducer" molecule
    one part extended for transient binding of DNA probes and subsequent sub-wavelength localization (i.e. ~1 nm localization accuracy, green dye)
    another part extended for stable hybridization for intensity barcode molecule (i.e. self-assembled DNA origami barcode (red and blue dyes))
  Localization microscopy of "start" and "end" biotinylated DNA strand used for subsequent spatial sequence mapping
  Detection of multiple stretched molecules using a widefield microscopy setup for complete coverage of target molecule sequence identification In some embodiments the transducer that labels the single stranded sequences are pre-labeled with the identification and localization tag.

In a preferred embodiment, the method of the present invention is used for the sequencing of genomic DNA molecules of arbitrary length and sequence composition.

The target DNA is stretched on a surface. 6-mer DNA transducer molecules "call" a 6 base target sequence using hybridization or ligation of phosphate modified 5'-end, transducer sequence extension at 3'-end contains localization tag and identification tag sequence. 5-mer DNA transducer molecules "call" a 5 base target sequence using ligation of phosphate modified 5'-end, transducer sequence extension at 3'-end contains localization tag and identification tag sequence.

The 5mer or 6mer transducer molecules can contain additional degenerate (N) or universal base positions. For example in a preferred embodiment a 5mer sequence has an additional degenerate base at each end.

In some embodiments, contiguous transducers ligate along a target nucleic acid sequence to enable read-out of the contiguous target sequence. This sequence may be a stretch of two or more transducers.

In one embodiment, the localization tag comprises a fluorophore which excites light in the blue range ("BLUE"). The identification tags comprise capture-sequence specific barcodes, such as sequence ACTG→"GREEN-RED-RED" and TGCC→"RED-GREEN-GREEN".

In some embodiments a plurality of capture (probes or target interrogation) sequences, each specific to a different target sequence are added simultaneously. In some embodiments the plurality of capture sequences comprises a complete repertoire of sequences. For example, the repertoire may comprise every possible 5mer or every possible 6mer.

In some embodiments the plurality of capture sequences each specific to a different target sequence comprise a panel of probes targeting specific sequences, for example mutations in BRCA1 or some other cancer gene, or genes that are responsible for genetic diseases such as CFTR, responsible for Cystic Fibrosis. Such genes are characterized by having the potential for multiple mutations and multiple sites would need to be interrogated for profiling the gene and performing a diagnostic.

The ease of use of the invention would make it adaptable to non-laboratory settings such as a hospital, clinic or doctor's office.

In addition to detecting point mutations the long range-view provided by stretched DNA molecules would allow the present invention to detect structural variations.

In addition, when applied to RNA, which typically are naturally single stranded the invention would allow the structure of alternative splicing isoforms of mRNA to be determined. For example, each exon could be bound to one or more capture (probe) sequences which are identified and localized by the methods of this invention. For example, the presence and location of each possible exon out of say, 20 can be determined. In some embodiments a small nucleotide detection entity is particularly useful for detecting multiple sequences (e.g. exons) on RNA; such entities many comprise a sub-fragment of a typical DNA origami based on M13 folding or a different type of nanostructure capable of being encoded.

In cases where the nucleotide detection entity is too large, for several of them to fit within a nucleic acid target segment, the nucleotide detection entities for each of the too-closely spaced target sites can be bound and removed, one after the other. While each nucleotide detection entity is bound its precise location can be identified by the transient binding of the localization tag to the localization sequence. Hence by precise nanometric localization, the location and identity of multiple closely spaced sequences (e.g. exon) can be determined. The removal of each nucleic acid detection entity can be conducted by heat and/or chemical denaturation or by its displacement by a probe (e.g. more stable or longer) sequence which does not contain the bulk of the nucleotide detection entity (neither the localization or identification sequence). Hence, after the nucleotide detection entity has been used to determine location and entity it is removed by adding the displacement probe which carries no detectable element and hence does not interfere with the probing of an adjacent sequence by a nucleotide detection entity. Alternatively, the nucleic acid detection entity has a cleavable moiety between the probe/capture sequence and the localization sequence. After detection and localization has been carried out the cleavable moiety is cleaved and all except the localization and identification parts are detached from the probe and allowed to diffuse away. The cleavable entity may be chemically cleavable, for example a disulphide linkage can be inserted during oligonucleotide synthesis and can be cleaved using a reducing agent (e.g. TCEP); a photocleavable moiety (e.g. 2-nitrobenzyl) can alternatively be inserted during oligonucleotide synthesis and can be cleaved by UV light.

In some embodiments the capture (probe) sequence is a guide RNA (gRNA) and a cas9 protein is provided to enable binding to a double stranded (non-nicked) target nucleic acid. In some embodiments the localization sequence and the identification sequence are at the 3' end of the guide RNA. In preferred embodiments the localization sequence is at the 5' end of the guide RNA and the identification sequence is at the 5' end of the localization sequence or is at the 3' end of the guide RNA.

The invention is particularly remarkable and outstanding because of the nucleotide localization sequence, which allows nanometric localization One advantage of the approach for many applications is, that the assay is simple. The target molecules are laid out on a 2-D surface, preferably stretched. One set of reagents (e.g. sequence specifically targeting a panel of exons) can all be added in one step followed by imaging.

For full sequence determination (e.g. of a genome or a RNA population, either a complete repertoire of nucleic acid detection entities is applied to an array of target nucleic acids, a sub-set of sequences are bound, and the nanometric location and identity of barcodes are recorded. Then the nucleic acid detection entities are removed, e.g. by heat and/or chemical denaturation. The binding, recording and removal is then repeated a sufficient number of times (e.g. 10-100×) so that all the sequence of the target nucleic acids is covered. In this embodiment one or more copies of the genome or nucleic acid sequence to be determined is provided. In another embodiment, the complete repertoire is only bound and imaged once, but a large number of copies (e.g. 100-20,000) of the target nucleic acid are present on the surface. In the case where several thousand copies need to be analyzed, 2-D translation of the sample stage with respect to the imaging device may be needed to gather sufficient data. In some embodiments it is preferable to use an imaging device (e.g. CMOS chip) with a large number of pixels, e g 5 million or more, coupled with high NA, low magnification objective lens, e.g. a 60×TIRF objective. As an alternative to Objective style TIRF, PRISM style TIRF can be used allowing use of a lower magnification (e.g. 20× or 40×) non-oil objective lens.

When DNA origami or similar nanostructures are used a very large number of distinct tags or barcodes can be created, e.g. 1024 for detecting a 5 base sequence or 4096 for a 6 base sequence.

For sample applications, such as the analysis of RNA molecules which are typically shorter than genomic DNA molecules, small nucleic acid detection entities can be used, so that many more can be packed in over a length of a few hundred or thousands of bases of a RNA transcript.

The following examples and drawings illustrate the present invention without, however, limiting the same thereto.

Experimental Methods

Extracting and Elongating Megabase Range Genomic DNA on a Surface

A number of methods exist for extracting and stretching High Molecular weight (HMW) or long length DNA. A Molecular Combing (Allemand et al Biophysical Journal 73:2064-2070 1997; Michalet et al Science 277:1518-1523 (1999)) protocol adapted from Kaykov et al (Scientific Reports 6:19636 2016) can be used to extract and elongate DNA with average lengths in the mega-base range. Genomic DNA is extracted from cells ($1 \times 10^4$ to $10^5$ per block) in agarose blocks (e.g. using Biorad or Genomic Vision protocol or as described by Kaykov et al) using Proteinase K for 1 hour, the washing step includes 100 mM NaCl, the agarose block is melted and digested in a trough using Beta-Agarase (NEB, USA) for an extended period (e.g. 16 hrs) at 42 degrees without mixing and then brought to room temperature. DNA is combed in a buffer containing 50 mM MES 100 mM of NaCl at pH 6. A device that can pull a substrate (e.g. coverglass) out of a trough (e.g. as described by Kaykov) is used to generate smooth, low friction z movement with minimal vibration. A combing speed of 900 μm/second is used to uniformly stretched DNA molecules with minimum breaking. Around 50% of the molecules are longer than 1 Mb with an average of 2 Mb in length and 5% over 4 MB.

The DNA on the coverglass is crosslinked to the surface using an energy of 10,000 microJoules using a crosslinker (Stratagene, USA).

In addition to fluidic approaches, polynucleotides (RNA/DNA) can be stretched by using an electric field using protocols described by Giess et al. Several approaches are available for elongating polynucleotides when they are not attached to a surface (e.g. Frietag et al; Marie et al).

Making the Flow Cell

The cover glass is pressed onto a flow cell gasket fashioned from double sided sticky 3M sheet which has already been attached to a glass slide. The gasket (with both sides of the protective layer on the double-sided sticky sheet on) is fashioned, using a laser cutter, to produce one or more flow channels. The length of the flow channel is longer than the length of the cover glass, so that when the cover glass is placed at the center of the flow channel, the portions of the channel one at each end that are not covered by the cover glass can be used as inlets and outlet for dispensing fluids into and out of the flow channel, such fluids passing atop the elongated polynucleotides on the vinyl silane surface). The fluids can be flowed through the channel by using safety swab sticks (Johnsons, USA) at one end to create suction as fluid is pipetted in at the other end. The channel is pre-wetted with PBS-Tween and PBS.

Alternatively, the DNA is not pre-stretched onto the cover glass, instead it is introduced into a pre-formed flow cell, bound to the surface at one end and stretched by applying a voltage across the flow cell, allowing the negatively charged nucleic acid backbone to align in one direction.

Stretching mRNA

One method for stretching RNA involves the provision of an oligo d(T) coated surface to which mRNA are hybridized and immobilized via the polyA tail. A plurality of nucleic acid detection entities are then bound to specific sequences on the mRNA (corresponding to specific exon sequences for example. The mRNA is then stretched by applying an electric field, as described by Giese et al. In some embodiments the nucleic acid detection entities contain oligonucleotide docking sites containing biotin, which after stretching can be affixed by interaction with streptavidin coated onto the surface. The streptavidin coating can be done by first coating with BSA-Biotin which is then bound to a streptavidin layer.

In some embodiments, a gene specific probe is hybridized to the immobilized RNA which is then hybridized to a structure for facilitating stretching, and optionally binding at the other end via a streptavidin-biotin interaction in a similar manner to that described by Giese et al, except that in the present invention the double stranded structure does not serve a reporter function; the reporter function is provided by the nucleic acid detection entities targeting specific exons. In some such embodiments the nucleic acid detection entities are bound after stretching of the mRNA.

Passivation

Before or after introduction of DNA the flow cell can be passivated by adding BSA, Caesin or Block-Aid (Thermofisher). Alternatively, the flow cell can be passivated using a lipid bilayer as described by Granelli et at or Persson et al.

Denaturing DNA

The double stranded DNA can be heat and/or chemical (e.g. denaturant comprising NaOH (e.g. 0.5M), Formamide, DMSO) denaturation.

Denaturing RNA

RNA has the potential to form secondary and tertiary structures, which need to be removed in order to stretch out the RNA. The structures can be removed by heat and or chemical (e.g. comprising Formamide, DMSO) denaturation.

Hybridizing Capture (Probe) Sequences

After the RNA or DNA have been denatured the capture (probe) sequences can be added into the flow cell or vessel. A temperature selected between 4 degrees and room temperature can be used in 4×SSC. The probe sequence can be modified with LNA and can contain a degenerate position at each end as described by Pihlak et al, with the Cy3 label being replaced by the localization/identification structure. Optionally, after one hybridization step, the bound molecules can be denatured, using heat, chemical denaturation or can be displaced by an unlabeled probe and another capture (probe) or set of capture (probes) can be added and repeated until the entire repertoire or panel has been used.

gRNA/Cas9 Binding

The CRISPR RNA/Protein system modified with nucleic acid detection entity sequence can be used to bind to selected sequences (e.g. for gRNA/cas9 a sequence adjacent to the PAM sequence). Reaction conditions described by Sternberg et al or in WO 2016/028843 A2.

Making Nicks in Double-Stranded DNA

After hydrating the stretched DNA with PBS. It is pre-conditioned with DNAse1 buffer. The DNAse1 reaction is undertaken, using 5 units DNAse 1 enzyme in DNAase1 buffer in a 20 ul reaction (Roche), the reaction is incubated at room temperature or 37 degrees for 10 minutes (or longer or shorter depending on the frequency of nicking required; the concentration of the DNAse1 is also adjusted accordingly). After nicking the DNAse1 is washed out by pipetting wash buffer (PBS, PBST) into the inlet at one end of the channel and using a tissue to blot out at the other end.

Ligating Capture (Probe) Sequences

Ligation can be carried out at the nicks by using T4 DNA ligase (e.g. NEB or Enzymatics) using vendor specified protocol. PEG may be used to speed up the reaction, as is found in Quick Ligation kit (NEB). In order of ligation to be carried out the capture probe may require a to have free 5 end which is phosphorylated (during oligo synthesis) or post-synthesis using Polynucleotide Kinase (NEB). The phosphorylated 5' end of the capture probe will ligate to a 3' termini of the nick. Alternatively, the capture probe carries a free 3' end and is ligated to a phosphorylated 5' end of the nick.

Depending on how the nick is created and whether 3' or 5' ligation is being carried out the stretched DNA may be exposed to polynucleotide kinase to phosphorylate 5' ends.

After nicking the cleaved ends are able to fray, especially when buffers containing low salt or denaturants such as formamide or DMSO are used. This facilitates the ligation of the capture (probe) sequence.

Staining the Polynucleotide

Optionally, for some embodiments, to trace out the backbone of a polynucleotide DNA stains and other polynucleotide binding reagents can be used. Intercalating dyes, major groove binders, labeled non-specific DNA binding proteins cationic conjugated polymers can be bound to the DNA. Intercalating dyes can be used at various nucleobase to dye ratios. Use of multiple intercalating dye donors at a dye to base pair ratio of about 1:5-10 leads to the labeling of DNA with dye molecules (e.g., Sybr Green 1, Sytox Green, YOYO-1) sufficient to serve as donors for nucleotide additions along the growing DNA strand. Some DNA binding reagents are able to substantially cover the polynucleotide.

Design of the DNA Origami Barcodes

Various types of supramolecular structures, such as DNA nanostructures (e.g. DNA Origami, DNA Bricks) can be used in the design of the identification part of the nucleic acid detection entities. For example, DNA origami barcodes can be designed according to Lin et al. In one such embodiment the main-body of the linear nano-barcode is a DNA six-helix-bundle (6 hb) nanorod. Staple strands representing barcode zones are extended at the 3'-end with single-stranded overhangs (handles) for super-resolution imaging using transient DNA binding microscopy.

The origami can be designed to have single-stranded overhangs or extensions (e.g. handles), where one end of a staple is integrated into the origami and the other end sticks out and is available for interaction. In one aspect of the invention the extension are biotinylated so that they can bind to streptavidin coated on the surface, so that the origami becomes well fixed to the surface once the nucleic acid detection entity has bound to the target nucleic acid. In some aspects, a non-biotinylated staple extension can be integrated into the origami, where the protruding part comprises the localization and probe sequence of the nucleic acid detection entity. Alternatively, the protruding part can hybridize to a connector sequence, which is attached to the localization sequence (see FIG. 7b). In this case the staple extension can be complementary to the origami connector sequence shown in 7b. The staple extension can be annealed to the connector before the nucleic acid detection entity is applied to the sample nucleic acids. Alternatively, the probe-localization-connector sequence is first ligated and/or hybridized to the target nucleic acid and then the DNA origami is bound to the connector via a staple extension.

Self-Assembly of the DNA Origami Barcodes

The assembly of the barcode is accomplished in a one-pot reaction by mixing 100 nM scaffold strands (e.g. 7,308-base long, termed p7308) derived from M13 bacteriophage with a pool of oligonucleotide staple strands (600 nM of each; reverse-phase cartridge purified.) in folding buffer containing 5 mM Tris, 1 mM EDTA, 20 mM $MgCl_2$, 50 mM NaCl (pH 8) and subjecting the mixture to a thermal-annealing ramp that cooled from 80° C. to 60° C. over the course of 80 minutes and then cooled from 60° C. to 24° C. over 15 hours. Excessive staples were removed from the folded nanorods by polyethylene glycol fractionation.

Transient Binding for Localization

The localization sequence and localization tags can comprise any pair of entities that can transiently bind to each other. In some embodiments the localization sequence is not a sequence but is a molecule that is part of a binding pair, that can be associated with or can form part of the localization detection entity. For example, the oligonucleotide synthesis needed to form the nucleotide detection entity can incorporate a biotin (via e.g. biotin-dT) which can transiently bind to an engineered low affinity streptavidin, low affinity monomer avidin, or to iminobiotin or desthiobiotin or to an anti-Biotin antibody (e.g. Biotin Monoclonal Antibody (BK-1/39), Alexa Fluor 488), under conditions that the binding is transient.

FIG. 7 presents a list of exemplary localization sequence-localization tag pairs. Any of the pairs can be used for localization. In particular partner 1a can be used with partner 1b where partner 1b bears a Cy3B label. The localization is carried out by providing the tags at ~5-10 nM concentration at room temperature in a buffer comprising: 5 mM Tris-HCl, 10 mM $MgCl_2$, 1 mM EDTA, 0.05% Tween-20, pH 8.

Optical Imaging

Fluorescence imaging for single molecule localization, when the localization tag is labeled with Cy3B is carried out on an inverted Nikon Eclipse Ti microscope (Nikon Instruments) with the Perfect Focus System, applying an objective-type TIRF configuration using a Nikon TIRF illuminator with an oil-immersion objective (CFI Apo TIRF 100×, NA 1.49, Oil). An additional 1.5 magnification is used to obtain a final magnification of ~150×, corresponding to a pixel size of 107 nm. For illumination a single 532 nm laser fiber is passed through a fiber optic scrambler (Point Source Inc) to obtain well homogenized illumination after optically coupling to the Nikon Ti TIRF attachment. Excitation and emission is done through 475/532/660 multichroic and 532 nm longpass filter and (Chroma) and the images are taken with a Hamamatsu ImageEM camera with a 50-200 ms exposure and either no EM gain or a level of EM gain where the noise is not too high. Typically, 5000 or more imaging frames are taken. The number of frames influences the accuracy of localization, with >10,000 frames and high numbers of photons collected suitable for down to a few nanometer and sub-nanometer localization (See Dai, Jungmann and Yin). Whereas, <10,000 frames is typically sufficient for localization to 10 or 20 nm, given sufficient photon collection.

For detection of the identification tags, depending on the labels or fluorophores used for coding the tag, blue (475 or 488 nm), green (532 nm, 543 nm, or 561n) and red lasers (633 nm, 640 nm, 660 nm) can be coupled into the fiber optic. Excitation, emission, and dichroic/multichroic filters can be purchased from Chroma inc, appropriate to the laser and dye combination used. Atto 488, Cy3B, Atto 655 are examples of dyes that are appropriate to use.

The microscope is controlled by Nikon Nis-Elements software using a high performance computer comprising for example, a Dell or Lenovo computer with a Xeon processor, 32 Gb RAM and a RAID array or solid state memory.

Image Analysis

ImageJ/Fiji and several other commercial or free software offer facilities for analysis of images. The single molecule localization methods provide an explicit list of position of signals on a 2-D surface. A a plug-in for ImageJ/Fiji, ThunderSTORM can be used for single molecule localization. Drift correction is of utmost importance for single molecule localization so the first step is drift correction and this is integrated into the localization software. e.g. ThunderSTORM. A Lenovo D30 Computer with Xeon processor and 32 Gb RAM for processing the single molecule localization software.

Resources that compare the various single molecule localization software are available (Sage et al).

Optionally DNA origami (~100 pM) drift markers or gold nanoparticles (~10 nM) can be added to the experiment as fiduciary markers which aid drift correction.

(A) The method of the invention uses the transient binding of a short fluorescently labeled DNA strand to a complementary handle strand, which is attached to the subunit or subunits under investigation for localization (which is bound to the target nucleic acid sequence being identified and localized). A distinct fluorophore, optically detectable particle or molecular barcode is used for subunit identification (shown as Sequence #124 in the blow-up).

(B) In some embodiments super-resolution imaging can be used to identify more compact barcodes, i.e. with higher information density.

(C) A stretch of target nucleic acid with several barcodes and localization tags. The barcodes can be aligned in parallel as seen here.

Figure 1A:
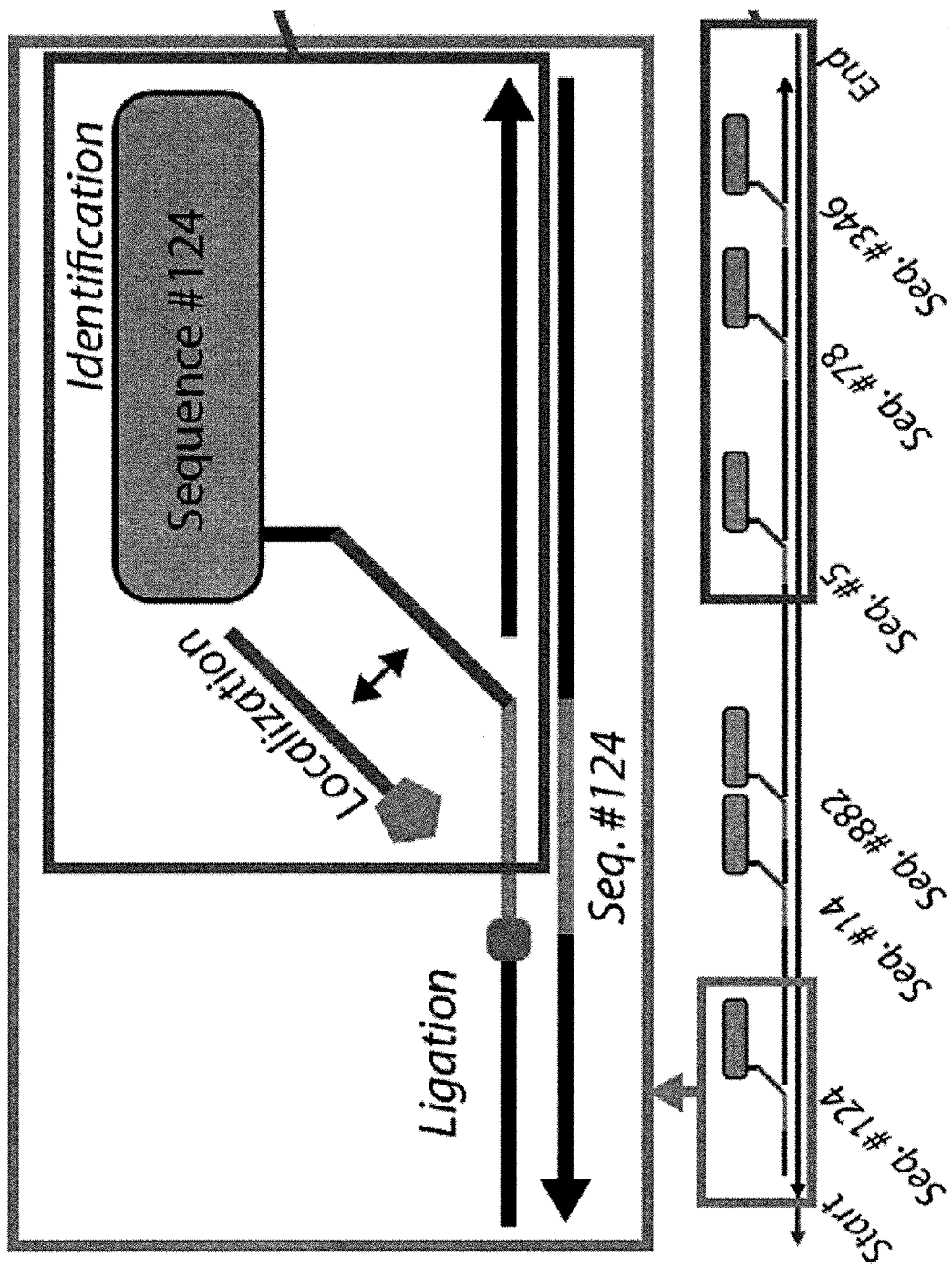
FIG. 1: Embodiment of nucleic acid sequencing. i.e. the determination of the nucleotide sequence of a strand of genomic DNA. Here, the method of the invention allows determining the identity (A, C, G or T) and order of every single nucleotide, the molecular subunit.
Figure 2:
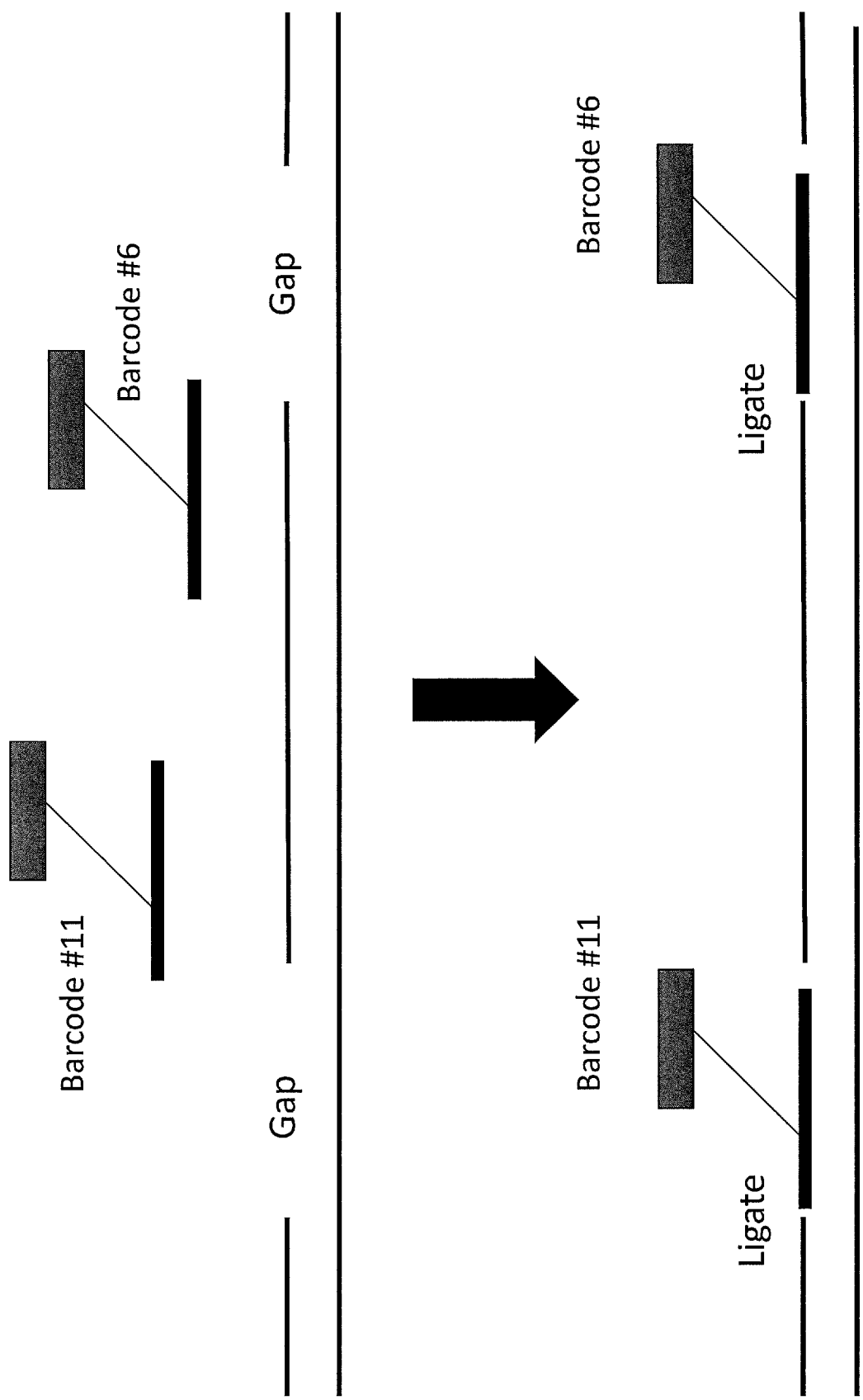

FIG. 2: Schematic showing ligation of nucleic acid detection entities to single stranded gaps in a stretched partially double stranded target nucleic acid. The gaps may be created by partial denaturation of the target nucleic acid duplex, strand invasion of the target nucleic acid duplex or fraying of the strands from nicks on a target nucleic acid duplex. The barcodes identify the target nucleic acid sequence and the localization sequence and localization tag (both not shown) determine the location on the target nucleic acid.

Figure 3:
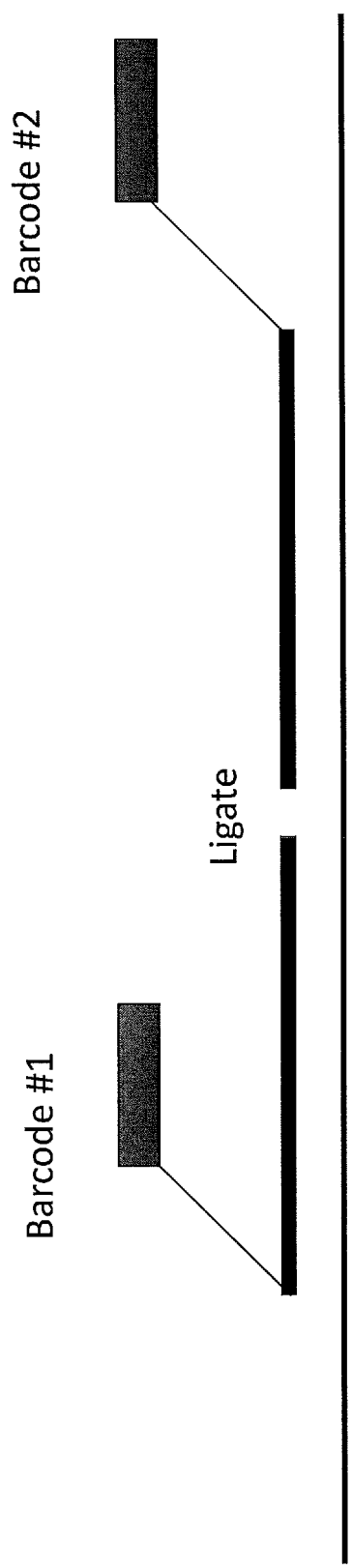

FIG. 3: Schematic showing ligation of two nucleic acid detection entities to adjacent locations on a target nucleic acid. The barcodes identify the target nucleic acid sequence and the localization sequence and localization tag (both not shown) determine the location on the target nucleic acid.

Figure 4:
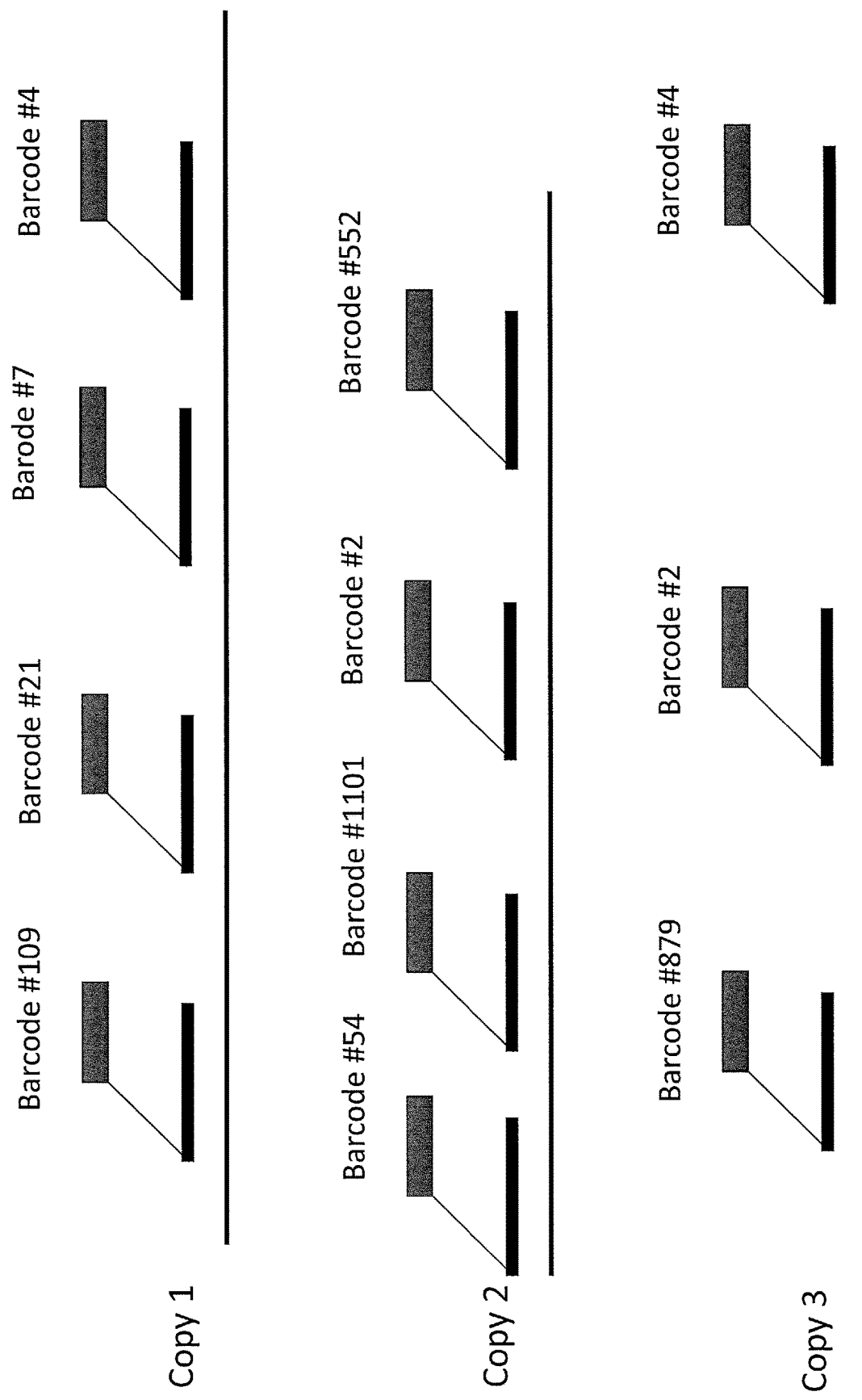

FIG. 4: Schematic showing hybridization of a repertoire of nucleic acid detection entities to copies of stretched target nucleic acid. The barcodes identify the target nucleic acid sequence and the localization sequence and localization tag (both not shown) determine the location on the target nucleic acid. Some of the locations bound to on the target nucleic acid copies are common between the copies and some are distinct.

Figure 5:
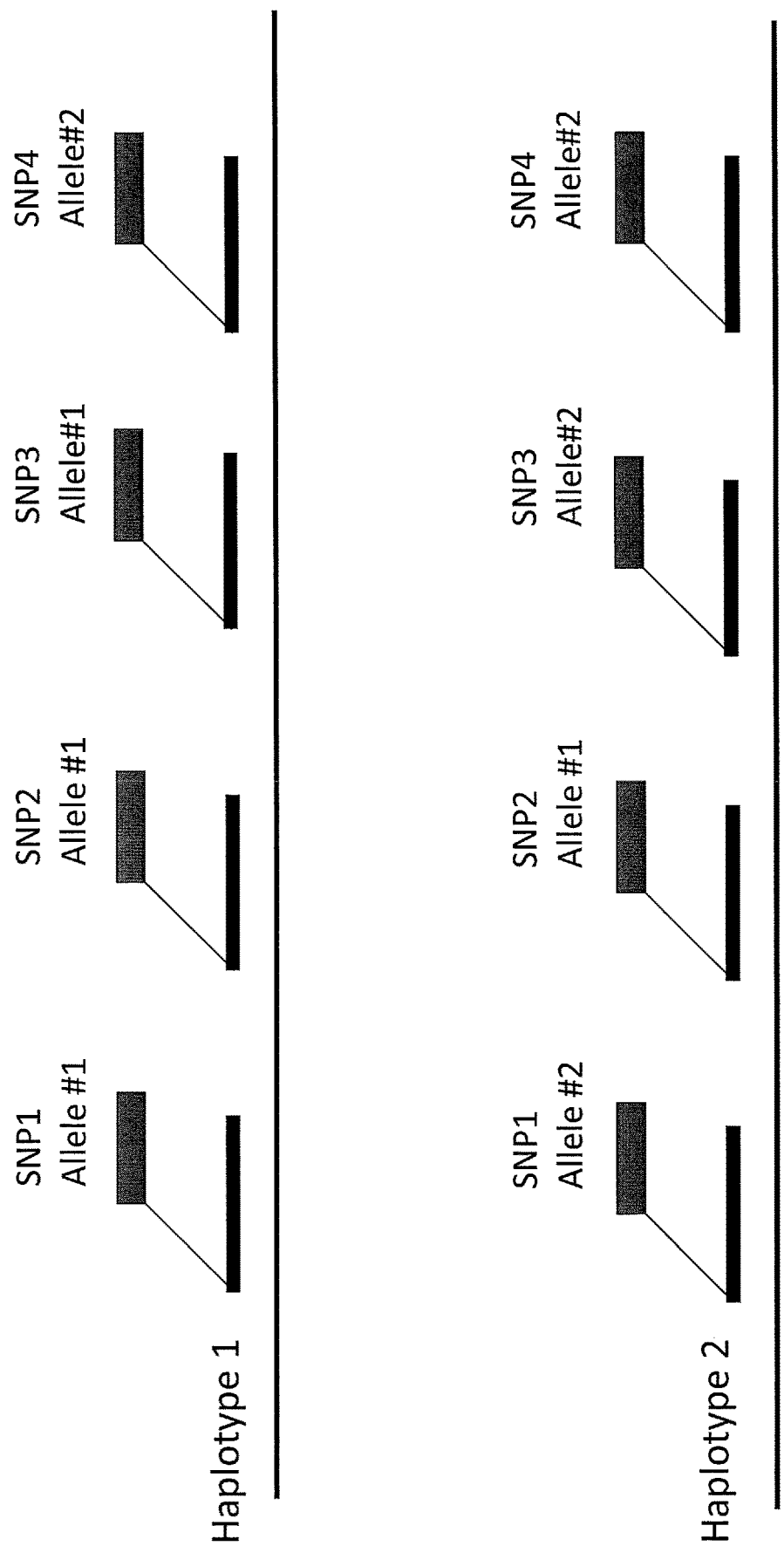

FIG. 5: Schematic showing hybridization of a panel of nucleic acid detection entities (e.g. SNP1 Allele #1) to different haplotypes of stretched target nucleic acid. The nucleic acid detection entities code for different alleles for each SNP in the panel. The nucleic acid detection entities identify the target nucleic acid sequence and the localization sequence and localization tag (both not shown) determine the location on the target nucleic acid. Instead of SNPs, the nucleic acid detection entities can be designed to target different mutations in a panel, for example mutations in the BRCA1 gene or the Cystic Fibrosis Transmembrane Receptor (CFTR).

Figure 6:
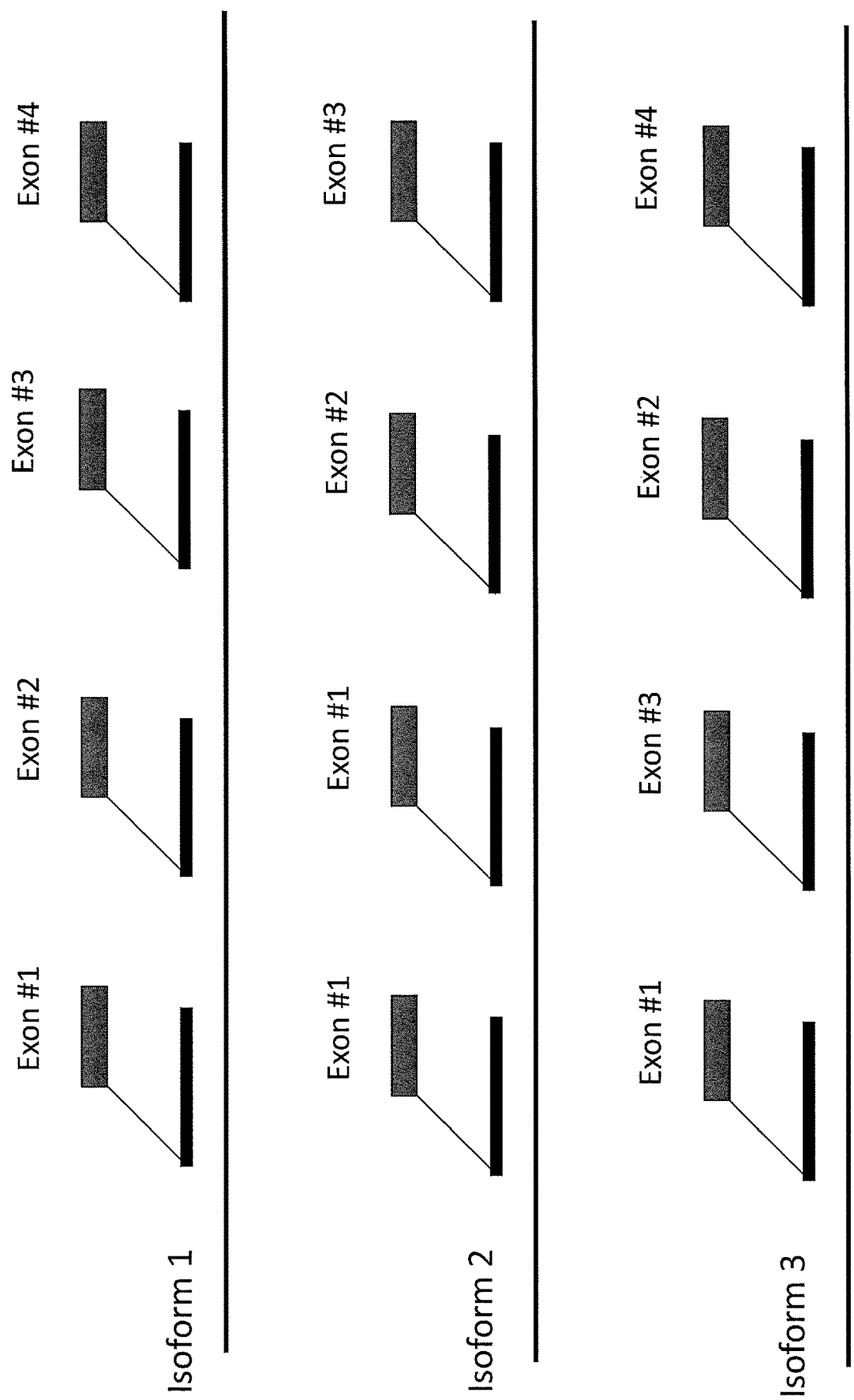

FIG. 6: Schematic showing hybridization of a panel of nucleic acid detection entities (e.g. Exon #1) to different isoforms of a stretched target nucleic acid transcript. The nucleic acid detection entities are specific for different exonic regions of the target nucleic acid transcript. The nucleic acid detection entities identify the target nucleic acid sequence and the localization sequence and localization tag (both not shown) determine the location on the target nucleic acid. Instead of SNPs, the nucleic acid detection entities can be designed to target different mutations in a panel, for example mutations in the BRCA1 gene or the Cystic Fibrosis Transmembrane Receptor (CFTR). Similarly, the structure of a long-range region of genomic DNA can be determined by using a panel of probes designed to mark particular genome segments.

FIG. 7: a. A list of sequence binding pairs that can be used as localization sequence (partner 1) and localization tag (partner 2). The localization sequences include partner 1a (SEQ ID NO: 1), 1b (SEQ ID NO: 3), 1c (SEQ ID NO: 5), 1d (SEQ ID NO: 7), 1e (SEQ ID NO: 9), 1f (SEQ ID NO: 11), 1g (SEQ ID NO: 13), 1h (SEQ ID NO: 15), 1i (SEQ ID NO: 17), 1j (SEQ ID NO: 19), 1k (SEQ ID NO: 21), and 1l (SEQ ID NO: 23) while the localization tags include partner 2a (SEQ ID NO: 2), 2b (SEQ ID NO: 4), 2c (SEQ ID NO: 6), 2d (SEQ ID NO: 8), 2e (SEQ ID NO: 10), 2f (SEQ ID NO: 12), 2g (SEQ ID NO: 14), 2h (SEQ ID NO: 16), 2i (SEQ ID NO: 18), 2j (SEQ ID NO: 20), 2k (SEQ ID NO: 22), and 2l (SEQ ID NO: 24). A set of pairs from this list can also be used to encode and detect the detection part—(e.g. Origami) of the nucleic acid detection entity when the nanostructure is designed to be encoded in a manner that requires superresolution (see Lin et al). b. An example of sequence components of nucleic acid detection entities. The probe sequence (SEQ ID NO: 25) is complementary to human centromeres, the localization sequence SEQ ID NO: 26) is complementary to localization tag 1b (FIG. 7a) and the connector sequence (SEQ ID NO: 27) is complementary to a staple extension that protrudes from the DNA origami; the three sequences are contiguous or may contain linker moieties in between. Such origami is of any one of the types described in Lin et al.

The features disclosed in the foregoing description, in the claims and/or in the accompanying drawings may, both separately and in any combination thereof, be material for realizing the invention in diverse forms thereof.

REFERENCES

Dai, Jungmann and Yin, Optical imaging of individual biomolecules in densely packed clusters. Nature Nanotechnology 11, 798-807 (2016)

Dietz, H., Douglas, S. M. & Shih, W. M. Folding DNA into Twisted and Curved Nanoscale Shapes. Science 325, 725-730 (2009).

Douglas, S. M. et al. Self-assembly of DNA into nanoscale three-dimensional shapes. Nature 459, 414-418 (2009).

Freitag C et al. Visualizing the entire DNA from a chromosome in a single frame. Biomicrofluidics. 9(4):044114 (2015)

Giess et al. Direct multiplexed measurement of gene expression with color-coded probe pairs. Nature Biotechnology 26, 317-325 (2008).

Granéli Al, Yeykal C C, Prasad T K, Greene E C. Organized arrays of individual DNA molecules tethered to supported lipid bilayers. Langmuir. 22:292-9 (2006).

Jungmann R, Steinhauer C, Scheible M, Kuzyk A, Tinnefeld P, Simmel F C. Single-molecule kinetics and super-resolution microscopy by fluorescence imaging of transient binding on DNA origami. Nano Lett. 201; 10(11): 4756-61. doi: 10.1021/nl103427w.

Jungmann R, Avendaflo M S, Woehrstein J B, Dai M, Shih W M, Yin P. Multiplexed 3D cellular super-resolution imaging with DNA-PANT and Exchange-PAINT. Nat Methods. 2014; 11(3):313-8. doi: 10.1038/nmeth.2835.

Lin C, Jungmann R, Leifer A M, Li C, Levner D, Church G M, Shih W M, Yin P. Submicrometre geometrically encoded fluorescent barcodes self-assembled from DNA. Nat Chem. 2012; 4(10):832-9.

Marie R, et al. Integrated view of genome structure and sequence of a single DNA molecule in a nanofluidic device. Proc Natl Acad Sci USA. 110:4893-8 (2013)

Persson, F., J. Fritzsche, K. U. Mir, M Modesti, F. Westerlund and J. O. Tegenfeldt. Lipid Passivation in Nanofluidics. Nanoletters, 12:2260-5 (2012).

Pihlak, A et al. Rapid genome sequencing with short universal tiling probes. Nature Biotechnology 26, 676-684 (2008).

Rothemund, P. W. K. Folding DNA to create nanoscale shapes and patterns. Nature 440, 297-302 (2006).

Sage et al., 2015 Quantitative evaluation of software packages for single-molecule localization microscopy. Nature Methods; http://bigwww.epfl.ch/smlm/software/).

Sternberg S H, Redding S, Jinek M, Green E C, Doudna J A. DNA interrogation by the CRISPR RNA-guided endonuclease Cas9. Nature 2014; 507: 62-67.

Yildiz A, Selvin P R. Fluorescence imaging with one nanometer accuracy: application to molecular motors. Acc Chem Res. 2005; 38(7):574-82.

The invention claimed is:

1. A method of determining the sequence of nucleotides in a target nucleic acid molecule comprising the steps of:
   (1) providing a target nucleic acid molecule, wherein copies of the target nucleic acid molecule are immobilized on a solid substrate,
   (2) providing a plurality of nucleic acid detection entities, wherein each nucleic acid detection entity is at least in part single stranded and comprises:
      (i) a specific probe nucleotide sequence,
      (ii) a localization nucleotide sequence for transient binding of a localization tag, and
      (iii) an identification nucleotide sequence for stable hybridization with an identification tag specific for the specific probe nucleotide sequence (i),
   (3) providing a plurality of identification tags, wherein each identification tag
      is specific for a specific probe nucleotide sequence (i) of the nucleic acid detection entity, and
      comprises a nucleotide sequence complementary to the identification nucleotide sequence (iii) of the nucleic acid detection entity,
   (4) providing a plurality of localization tags, wherein said localization tag comprises
      a nucleotide sequence complementary to the localization nucleotide sequence (ii) of the nucleic acid detection entity, and
      marker(s) or label(s),
   (5) hybridizing and optionally ligating the nucleic acid detection entities to a single strand of the target nucleic acid molecules,
   (6) hybridizing the identification tags to the identification nucleotide sequence (iii) of the nucleic acid detection entities,
      optionally, stretching and/or aligning the identification nucleotide sequence (iii) of the nucleic acid detection entities,
   (7) detecting the identification tags,
   (8) transiently hybridizing the localization tags, to the localization nucleotide sequence (ii) of the nucleic acid detection entities and detecting said transient hybridization, and
   (9) spatially detecting and identifying the nucleic acid sequence in the target nucleic acid molecules.

2. The method of claim 1, wherein the target nucleic acid molecule is dsDNA, ssDNA, dsRNA, ssRNA or a chimera or analogue thereof.

3. The method of claim 1, wherein a plurality of copies of the target nucleic acid molecule is provided.

4. The method of claim 1, wherein the target nucleic acid molecule is attached or immobilized to the solid substrate via
   biotin/streptavidin,
   chemical linking,
   molecular combing,
   electrostatic interaction,
wherein said substrate is optionally pre-coated with a chemical or biological coating.

5. The method of claim 1, wherein the target nucleic acid molecule is stretched
   (a) randomly but aligned in parallel to other copies of the target nucleic acid molecule;
   (b) in the form of a DNA curtain;
   (c) randomly;
   (d) via molecular combing;
   (e) via flow stretching; or
   (f) via nano confinement.

6. The method of claim 1, wherein double-stranded target nucleic acid molecules are rendered into single stranded target nucleic acid molecules.

7. The method of claim 6, wherein double-stranded target nucleic acid molecules are rendered into fully or partially single stranded target nucleic acid molecules as part of step (1),
   via
      enzymes,
      melting, or
      chemical denaturation.

8. The method of claim 1, wherein the specific nucleotide sequence (i) of a nucleic acid detection entity has a length of about 3 to 30 nucleotides.

9. The method of claim 1, wherein the identification nucleotide sequence (iii) of a nucleic acid detection entity has a length of about 5 to 100 nucleotides.

10. The method of claim 1, wherein the identification tags are—labelled DNA origami probes.

11. The method, according to claim 10, wherein the identification tags are labelled DNA origami molecules comprising a fluorescence barcode.

12. The method of claim 1, wherein the solid substrate is glass, silicon, silicon dioxide, Polydimethoxysilane (PDMS), polymer or a metal.

13. The method of claim 1, wherein the marker or label of the localization tags are
   fluorophore(s),
   detectable (nano)particle(s),
   latex (nano)particles,
   quantum dot(s), or
   combinations thereof.

14. The method of claim 1, wherein the accuracy or resolution limit of the method is ≤1 nm.

15. The method of claim 1, wherein step (5) comprises the use of a guide RNA.

16. The method, according to claim 1, wherein the immobilized target nucleic acid molecules are stretched.

17. The method, according to claim 1, wherein each identification tag is, or can be, detectably labeled.

18. The method, according to claim 1, which comprises applying a plurality of identical localization tags.

19. The method, according to claim 1, which comprises, in Step (5), hybridizing the nucleic acid detection entities to the single stranded target nucleic acid molecules and optionally ligating the nucleic acid detection entities to a nucleic acid annealed to the single stranded target nucleic acid.

20. The method, according to claim 1, which comprises detecting the identification tags via fluorescence microscopy or high resolution microscopy.

* * * * *

SEQUENCE LISTING

<160> NUMBER OF SEQ ID NOS: 27

<210> SEQ ID NO 1
<211> LENGTH: 11
<212> TYPE: DNA
<213> ORGANISM: Artificial Sequence

```
<220> FEATURE:
<223> OTHER INFORMATION: localization sequence

<400> SEQUENCE: 1
ttatacatct a                                                              11

<210> SEQ ID NO 2
<211> LENGTH: 10
<212> TYPE: DNA
<213> ORGANISM: Artificial Sequence
<220> FEATURE:
<223> OTHER INFORMATION: Localization Tag, label at 3' end

<400> SEQUENCE: 2
ctagatgtat                                                                10

<210> SEQ ID NO 3
<211> LENGTH: 11
<212> TYPE: DNA
<213> ORGANISM: Artificial Sequence
<220> FEATURE:
<223> OTHER INFORMATION: Localization Sequence

<400> SEQUENCE: 3
ttatctacat a                                                              11

<210> SEQ ID NO 4
<211> LENGTH: 10
<212> TYPE: DNA
<213> ORGANISM: Artificial Sequence
<220> FEATURE:
<223> OTHER INFORMATION: Localization tag labeled at 3' end

<400> SEQUENCE: 4
tatgtagatc                                                                10

<210> SEQ ID NO 5
<211> LENGTH: 11
<212> TYPE: DNA
<213> ORGANISM: Artificial Sequence
<220> FEATURE:
<223> OTHER INFORMATION: Localization Sequence

<400> SEQUENCE: 5
tttcttcatt a                                                              11

<210> SEQ ID NO 6
<211> LENGTH: 10
<212> TYPE: DNA
<213> ORGANISM: Artificial Sequence
<220> FEATURE:
<223> OTHER INFORMATION: Localization Tag labeled at 3' end

<400> SEQUENCE: 6
gtaatgaaga                                                                10

<210> SEQ ID NO 7
<211> LENGTH: 11
<212> TYPE: DNA
<213> ORGANISM: Artificial Sequence
<220> FEATURE:
<223> OTHER INFORMATION: Localization Sequence

<400> SEQUENCE: 7
ttatgaatct a                                                              11
```

```
<210> SEQ ID NO 8
<211> LENGTH: 10
<212> TYPE: DNA
<213> ORGANISM: Artificial Sequence
<220> FEATURE:
<223> OTHER INFORMATION: Localization Tag labeled at 3' end

<400> SEQUENCE: 8
gtagattcat                                                                10

<210> SEQ ID NO 9
<211> LENGTH: 11
<212> TYPE: DNA
<213> ORGANISM: Artificial Sequence
<220> FEATURE:
<223> OTHER INFORMATION: Localization Sequence

<400> SEQUENCE: 9
ttttaggtaa a                                                              11

<210> SEQ ID NO 10
<211> LENGTH: 10
<212> TYPE: DNA
<213> ORGANISM: Artificial Sequence
<220> FEATURE:
<223> OTHER INFORMATION: Localization Tag labeled at 3' end

<400> SEQUENCE: 10
ctttacctaa                                                                10

<210> SEQ ID NO 11
<211> LENGTH: 11
<212> TYPE: DNA
<213> ORGANISM: Artificial Sequence
<220> FEATURE:
<223> OTHER INFORMATION: Localization Sequence

<400> SEQUENCE: 11
ttaattgagt a                                                              11

<210> SEQ ID NO 12
<211> LENGTH: 10
<212> TYPE: DNA
<213> ORGANISM: Artificial Sequence
<220> FEATURE:
<223> OTHER INFORMATION: Localization Tag labeled at 3' end

<400> SEQUENCE: 12
gtactcaatt                                                                10

<210> SEQ ID NO 13
<211> LENGTH: 11
<212> TYPE: DNA
<213> ORGANISM: Artificial Sequence
<220> FEATURE:
<223> OTHER INFORMATION: Localization Sequence

<400> SEQUENCE: 13
ttaattagga t                                                              11

<210> SEQ ID NO 14
<211> LENGTH: 10
<212> TYPE: DNA
<213> ORGANISM: Artificial Sequence
<220> FEATURE:
<223> OTHER INFORMATION: Localization Tag labeled at 3' end
```

```
<400> SEQUENCE: 14
catcctaatt                                                              10

<210> SEQ ID NO 15
<211> LENGTH: 11
<212> TYPE: DNA
<213> ORGANISM: Artificial Sequence
<220> FEATURE:
<223> OTHER INFORMATION: Localization Sequence

<400> SEQUENCE: 15
ttataatgga t                                                            11

<210> SEQ ID NO 16
<211> LENGTH: 10
<212> TYPE: DNA
<213> ORGANISM: Artificial Sequence
<220> FEATURE:
<223> OTHER INFORMATION: Localization Tag labeled at 3' end

<400> SEQUENCE: 16
gatccattat                                                              10

<210> SEQ ID NO 17
<211> LENGTH: 11
<212> TYPE: DNA
<213> ORGANISM: Artificial Sequence
<220> FEATURE:
<223> OTHER INFORMATION: Localization Sequence

<400> SEQUENCE: 17
tttaataagg t                                                            11

<210> SEQ ID NO 18
<211> LENGTH: 10
<212> TYPE: DNA
<213> ORGANISM: Artificial Sequence
<220> FEATURE:
<223> OTHER INFORMATION: Localization Tag labeled at 3' end

<400> SEQUENCE: 18
caccttatta                                                              10

<210> SEQ ID NO 19
<211> LENGTH: 11
<212> TYPE: DNA
<213> ORGANISM: Artificial Sequence
<220> FEATURE:
<223> OTHER INFORMATION: Localization Sequence

<400> SEQUENCE: 19
ttatagagaa g                                                            11

<210> SEQ ID NO 20
<211> LENGTH: 10
<212> TYPE: DNA
<213> ORGANISM: Artificial Sequence
<220> FEATURE:
<223> OTHER INFORMATION: Localization Tag labeled at 3' end

<400> SEQUENCE: 20
ccttctctat                                                              10

<210> SEQ ID NO 21
```

```
<211> LENGTH: 11
<212> TYPE: DNA
<213> ORGANISM: Artificial Sequence
<220> FEATURE:
<223> OTHER INFORMATION: Localization Sequence

<400> SEQUENCE: 21
ttttgatgat a                                                              11

<210> SEQ ID NO 22
<211> LENGTH: 10
<212> TYPE: DNA
<213> ORGANISM: Artificial Sequence
<220> FEATURE:
<223> OTHER INFORMATION: Localization Tag labeled at 3' end

<400> SEQUENCE: 22
gtatcatcaa                                                                10

<210> SEQ ID NO 23
<211> LENGTH: 11
<212> TYPE: DNA
<213> ORGANISM: Artificial Sequence
<220> FEATURE:
<223> OTHER INFORMATION: Localization Sequence

<400> SEQUENCE: 23
ttatagtgat t                                                              11

<210> SEQ ID NO 24
<211> LENGTH: 10
<212> TYPE: DNA
<213> ORGANISM: Artificial Sequence
<220> FEATURE:
<223> OTHER INFORMATION: Localization Tag labeled at 3' end

<400> SEQUENCE: 24
gaatcactat                                                                10

<210> SEQ ID NO 25
<211> LENGTH: 32
<212> TYPE: DNA
<213> ORGANISM: Artificial Sequence
<220> FEATURE:
<223> OTHER INFORMATION: Centromere specific probe

<400> SEQUENCE: 25
tcacagagtt gaacgatcct ttacacagag ca                                       32

<210> SEQ ID NO 26
<211> LENGTH: 11
<212> TYPE: DNA
<213> ORGANISM: Artificial Sequence
<220> FEATURE:
<223> OTHER INFORMATION: Localization sequence

<400> SEQUENCE: 26
ttatacatct a                                                              11

<210> SEQ ID NO 27
<211> LENGTH: 25
<212> TYPE: DNA
<213> ORGANISM: Artificial Sequence
```

```
<220> FEATURE:
<223> OTHER INFORMATION: Origami connector

<400> SEQUENCE: 27
tatgaggacg aatctcccgc ttata                                            25
```